United States Patent [19]

Beitel

[11] 4,376,392

[45] Mar. 15, 1983

[54] VISCOUS SLUDGE SAMPLE COLLECTOR

[75] Inventor: George A. Beitel, Richland, Wash.

[73] Assignee: The United States of America as represented by the United States Department of Energy, Washington, D.C.

[21] Appl. No.: 291,898

[22] Filed: Aug. 11, 1981

[51] Int. Cl.³ .............................................. G01N 1/08
[52] U.S. Cl. ................................................. 73/864.45
[58] Field of Search ......................... 73/864.44, 864.45

[56] References Cited

U.S. PATENT DOCUMENTS 3,412,814 11/1968 Rosfelder ......................... 73/864.45

FOREIGN PATENT DOCUMENTS 2131955 12/1972 Fed. Rep. of Germany ... 73/864.45

OTHER PUBLICATIONS

Piggot, C. S., *Bulletin of the Geological Society of America*, vol. 47, May 31, 1936, pp. 675–684.
Design News, 3/9/81, p. 22.
Andresen, A. et al, *Proc. 6th Internat. Conf. Soil Mech.*, 1965.
Mackerath, F. J. H., Liminologn and Oceanography, vol. 3, 1958, pp. 181–191.

Primary Examiner—S. Clement Swisher
Attorney, Agent, or Firm—Douglas E. Erickson; Richard E. Constant; Richard G. Besha

[57] ABSTRACT

A vertical core sample collection system for viscous sludge. A sample tube's upper end has a flange and is attached to a piston. The tube and piston are located in the upper end of a bore in a housing. The bore's lower end leads outside the housing and has an inwardly extending rim. Compressed gas, from a storage cylinder, is quickly introduced into the bore's upper end to rapidly accelerate the piston and tube down the bore. The lower end of the tube has a high sludge entering velocity to obtain a full-length sludge sample without disturbing strata detail. The tube's downward motion is stopped when its upper end flange impacts against the bore's lower end inwardly extending rim.

10 Claims, 1 Drawing Figure

VISCOUS SLUDGE SAMPLE COLLECTOR

The United States Government has rights in this invention pursuant to Contract No. DE-AC06-77RL01030 between the U.S. Department of Energy and the Rockwell International Corporation.

BACKGROUND OF THE INVENTION

The present invention relates generally to core samplers and more particularly to a device for collecting vertical core samples of viscous sludge.

Viscous sludges include the semi-solid materials found at the bottom of nuclear waste, chemical, and petrochemical storage tanks, as well as the mud-like sediments found at the bottom of oceans, rivers, deep wells, etc. Wherever viscous sludge is found, it may be desirable or necessary to obtain a representative vertical core sample of it, with the sample retaining strata detail.

Existing sludge samplers, with the possible exception of the Piggot ocean-bottom sampler, may be classified as low velocity samplers in which a pipe or tube is pushed relatively slowly into the sludge, perhaps with some rotation. The push may come by hand, by repeatedly pounding the pipe with an appropriate driving mechanism, or by an expensive, complicated rotary core drilling machine or other apparatus designed for that purpose. Low velocity samplers, in the case of a highly viscous sludge, will have their sample tube plug up after penetrating a depth equal to a relatively low number of tube diameters, preventing the entrance of any additional material. Also, to the extent that the sludge is flowable, low velocity samplers will cause vertical mixing. For harder sludges, existing samplers cannot be pushed into the material because the required force will exceed the buckling resistance of the tubing.

The Piggot ocean-bottom sampler (*Bulletin of the Geological Society of America*, Vol. 47, May 31, 1936, pp. 675–684, 3 PLS., 1 FIG., Piggot, C. S., "Apparatus to Secure Core Samples From the Ocean-Bottom") appears to have a slowly descending brass sample tube and a surrounding steel bit tube at least contacting, and more likely partially penetrating, the ocean bottom at which time a self-contained, bottom-sensing inertia firing mechanism discharges a powder charge which drives the brass sample tube, steel bit tube, firing mechanism, and other components further into the mud to obtain a core sample. Because the sample tube does not maintain a high velocity throughout the sample collection, but starts by partially penetrating or contacting the mud at very low or zero velocity which then increases with the powder discharge, some vertical mixing of the sludge will occur, at least in the top portion of the sample. The ocean-bottom sampler appears unsuited for use in sampling the sludge of radioactive waste tanks because most of its reusable components, along with the sample tube, are driven into the contaminated sludge.

SUMMARY OF THE INVENTION

It is an object of this invention to provide a simple and inexpensive device, of small size, for quickly collecting a vertical core sample of a viscous sludge.

It is another object of the invention to collect a representative, long-lengthed, viscous sludge sample which retains complete strata information.

It is a further object of the invention to provide a sludge sampler which is remotely operated and suitable for use in a radioactive environment.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the vertical core sample collection system for viscous sludge may comprise a sample tube attached to a piston contained in a cylindrical bore of a housing. The housing may be positioned with the bore vertical and its lower, outside-leading end near the sludge. The tube and piston are temporarily maintained at the bore's upper end by a holding scheme. The tube is much shorter than the bore. There is a side vent in the bore's lower end and in the tube's upper end. An acceleration mechanism, preferably compressed gas from a storage cylinder, rapidly accelerates the piston and tube down the bore toward its lower end so that the tube enters the sludge with sufficient velocity to obtain a representative core sample. An outwardly projecting flange, preferably annular, on the tube's upper end guides it down the bore and stops the tube's motion, after the sample is collected, by encountering an inwardly projecting rim on the bore's lower end. Preferably the housing has a scheme to allow removal and reloading of the sample tube and the bore. This system is ideally used to sample radioactive sludge in a tank having an accessible top where the housing is remotely positioned by a hoist having a cable connected to lifting bails on the housing.

Several benefits and advantages are derived from the invention. Representative vertical cores of viscous sludges can be obtained retaining strata detail, and this can be done quickly by a simple, inexpensive device which can even be remotely operated in a radioactive environment.

BRIEF DESCRIPTION OF THE DRAWINGS

The accompanying drawing which is incorporated in and forms a part of this specification, illustrates one embodiment of the present invention and, together with a description, serves to explain the principles of the invention. In the drawing.

DETAILED DESCRIPTION OF THE INVENTION

Figure 1:
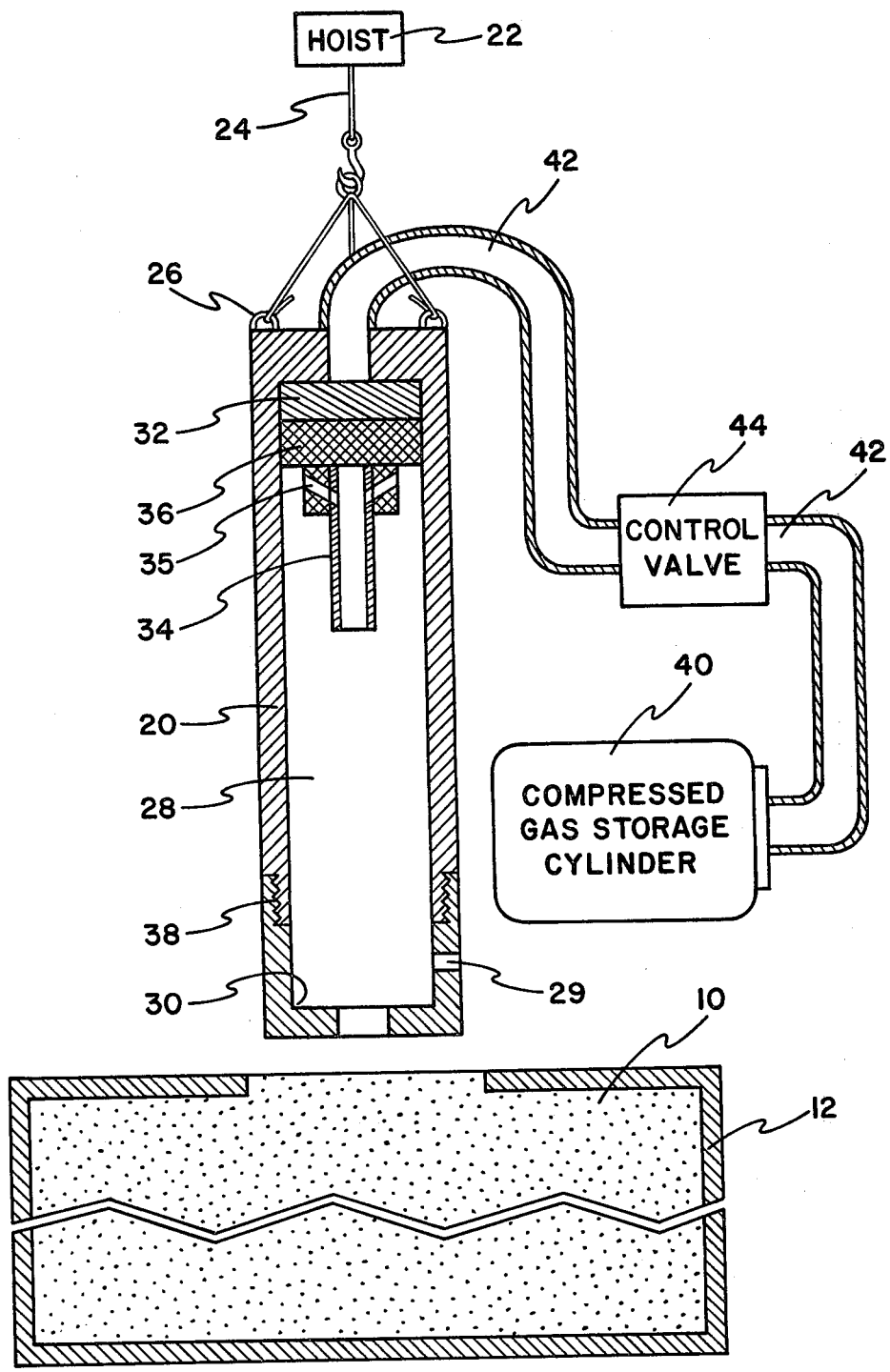
FIG. 1 is a cross sectional view of the sludge sampling system utilizing a compressed gas storage cylinder to accelerate the sample tube.

Reference will now be made in detail to a present preferred embodiment of the invention, an example of which is illustrated in the accompanying drawing.

FIG. 1 depicts the vertical core sample collection system utilized in a nuclear waste storage facility. Radioactive viscous sludge 10 is contained in a storage tank 12. A roof plate has been temporarily removed to allow access to the sludge 10 from the top of the tank 12.

In accordance with the invention, the sludge sampler's housing 20 is portable and supported in a vertical position by a remote positioning means, which preferably includes a hoist 22 acting through cables 24 attached to lifting bails 26 located on the upper portion of the housing 20. Other remote positioning means could include a crane, industrial robot or the like. In nonnuclear applications, the remote positioning means might not be needed, and the housing 20 could be manually positioned to rest on some support or even on the sludge itself. The housing 20 contains a right-circular, cylindrical bore 28. When the bore 28 is vertically oriented, the housing 20 is considered to be in a vertical position. The lower end of the bore 28 leads outside the housing 20 and this lower end terminates in an inwardly and perpendicularly extending ring-shaped rim 30.

In accordance with the invention, a movable piston 32 and a hollow sample tube 34 are coaxially placed in the bore 28. The upper part of the tube 34 has an outwardly and perpendicularly extending flange 36 which guides the tube 34 down the bore 28 and stops against the bore's rim 30. Preferably the flange 36 is annular in shape. The tube's upper part is connected to the bottom part of the piston 32. The tube 34, flange 36, and piston 32 could be made as a single unit (or permanently bonded as such) to be completely replaced for an additional sampling, or the tube 34 with flange 36 could be detachably connected to the piston 32 (by a threaded attachment for example), so that the piston could be reused. To allow additional sampling, with the same housing, the housing 20 has means for entering the bore 28 to load and unload the tube 34. Preferably such bore entry means includes a threaded attachment 38 whereby a lower portion of the housing is removably attached to the upper portion of the housing. Additional bore entry means include those used on firearms, military artillery, submarine torpedo tubes and the like.

The tube 34, with attached piston 32, has an initial position with its flange 36 near the bore's upper end, and a final position with its flange 36 contacting the rim 30 of the bore's lower end. In accordance with the invention, means are provided for temporarily holding the tube 34 at its initial position. Preferably such holding means include the removable piston 32 being slightly oversized and made of a compressible material to provide a snug fit within the bore 28 so that the piston 32 could hold up itself and the attached tube 34 with connected flange 36. Additional holding means include an "O" ring, attached to the bore near its upper end, to maintain the piston 32 or flange 36; a spring loaded transversely oriented pin, attached in the bore, having an inclined end obliquely facing the flange 36 and holding it from underneath until force is applied to the piston causing the flange to push the pin back against the spring and be released; and the like.

In accordance with the invention, means are also provided for rapidly accelerating the tube 34, via the piston 32, to move the tube 34 down the bore 28 such that when the tube's lower end reaches the sludge 10, the tube 34 will have a sufficient velocity to fully penetrate the sludge 10 and obtain a sludge sample which retains strata detail, before being stopped by the flange 36 - rim 30 contact. To achieve a sufficient tube sludge entering velocity even when the housing 20 is very near or contacts the sludge 10, the tube 34 is made substantially shorter than the bore 28 and should not be longer than about one half the length of the bore. Preferably the acceleration means include compressed gas, from a storage cylinder 40 which is rapidly introduced into the bore's upper end through an air hose 42 by a fast acting control valve 44. Alternately, the compressed gas could originate from a controlled chemical explosion where explosive chemicals are ignited and burned in the bore's upper part upon a signal from a control switch acting through a cable wire. What is required here is a subsonic reaction with peak pressures under one thousand psi. This is to be contrasted with a detonation which is associated with supersonic reaction rates and one million psi shock waves.

For efficient operation of the sludge sampler, the bore's lower end has one or more side vents 29 to minimize air resistance effects caused by the rim 30 when the tube 34 is accelerated down the bore 28. Also, the tube's upper part has one or more transverse side vents 35 to minimize air compression effects when the tube 34 moves through the sludge 10.

Successful operation of the sludge sampler requires the attainment of a high velocity for the sample tube 34 which must be maintained throughout the sample collection. Most sludges with a high viscosity and of a "sticky" consistency, are either Bingham plastic fluids or thixotropic fluids, and if the velocity were to exceed the inertial response of the media, a thin tube would encompass a core of the media before the media could move (except for the annular region immediately in front of the leading edge of the tube). For a sludge which would behave as a Newtonian fluid, flow into the pipe would be turbulent, resulting in transverse mixing only and hence strata information would be retained. It has been found that velocities between 40 and 60 meters per second are sufficient to obtain samples in sludge with a viscosity of $10^7$ centipoises using a 1.5 centimeter diameter sample tube. Velocities between 40 and 300 meters per second should be adequate to sample most sludge media.

The sample tube with a small diameter can capture a high viscosity sludge by inherent cohesiveness of the medium and does not require a mechanical closure prior to transport. The natural tendency of the highly viscous sludge to plug a small diameter tube prevents loss of the sample. In certain applications, it may be desired to temporarily seal the sample tube at the time of sampling. This can easily be done when the sample tube length is longer than the medium to be sampled by starting with a serated tube which will crimp shut when it strikes the sludge container bottom. This is easily and safely achieved in steel containers using a "soft" copper sample tube.

The sample tube dimensions may be chosen to be compatible with the total system. Sample tubes may be made of any material (aluminum, copper, brass, steel, stainless steel, titanium, etc.) chemically compatible with the material to be sampled. Copper or stainless steel tubing 1 to 2 centimeters in diameter having a wall thickness 0.05 to 0.2 centimeter is readily available, inexpensive, and well suited to most sampling needs. The sample tube length may be any convenient length which allows an adequate sample size to be obtained and is short enough to withstand the acceleration required to achieve the requisite velocities.

In a nonradioactive test of the sludge sampler, a copper tube was chosen about 1.3 meters long, 1.5 centimeters in (outside) diameter, and 0.1 centimeter in wall thickness. The tube was accelerated to have a sludge entering velocity of generally 50 meters per second. A 112 centimeter (44 inch) deep bed of bentonite clay based drilling mud with a consistency of a heavy wheel bearing grease was chosen as a highly viscous sludge having a viscosity approximately equal to $10^7$ centipoises. The sludge sampler collected 102 centimeters (40 inches) of sludge which represented over a 90% sample. When the tube was pushed in the sludge in a slow speed comparison test, without using the sludge sampler, only 5 centimeters (2 inches) of sludge was collected.

Sludge in nuclear waste tanks may be covered with a layer of liquid. In this case, the sludge sampler's housing 20 would be lowered through the liquid layer until the sludge layer was reached. The liquid could be kept out of the housing's bore 28 by capping the bore with an expendable foil or plastic seal which would rupture upon acceleration, or by other methods such as internally pressurizing the bore with gas to keep the waste liquid out.

After sampling, in the simplest set up, the sample is retrieved by withdrawing the sample tube 34. The sample may be sealed within the sample tube by the simple task of crimping the sample tube by either manual or remotely operated tube crimpers. Individual strata samples may be obtained and sealed by using a combination crimping/cutting action. Alternately, due to the tubular design of the invention, the sample tube 34 and contents can be withdrawn into a larger diameter tube or pipe and by means of standard valves sealed entry and exit can be provided. If radioactive materials are to be sampled, a minimum amount of shielding is required with the smaller diameter cylindrical geometry of the sample tube, to provide both radiation protection and containment.

The operation of the sludge sampler depicted in FIG. 1 is as follows. The housing 20 is lowered by the hoist 22 such that the bore 28 is held in a vertical position with its lower end near the top of the radioactive sludge 10. The control valve 44 is activated to propel the tube 34 into the sludge 10 to obtain a core sample. The hoist 22 then raises the housing and tube. Using appropriate shielding, if necessary, the tube 34 is cut near the bore's lower end and the uncontaminated tube portion remaining within the bore is removed from the bore 28 by unscrewing the bore's lower end. The cut tube 34 is then taken to be analyzed, a new tube is inserted in the bore, and the bore's lower end reattached to await the next sampling.

In summary, a viscous sludge vertical core sample may be collected by rapidly accelerating a sample tube down a bore to give the tube a high velocity to fully penetrate the sludge without disturbing the strata detail, and then by stopping the tube's motion with the tube's upper end outwardly projecting flange stopped against the bore's lower end inwardly projecting rim.

The foregoing description of a preferred embodiment of the invention has been presented for purposes of illustration and description. It is not intended to be exhaustive or to limit the invention in the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A vertical core sample collection system for viscous sludge, comprising:

(a) a housing having a right-circular, cylindrical bore, said bore having an upper end and a lower end, said lower end leading outside said housing, having a transverse vent, and terminating in a transversely and inwardly projecting annular rim, and said housing movable so that said bore is generally vertically disposable with said bore's lower end proximate said sludge to be sampled;

(b) a movable piston coaxially disposed in said bore and having an upper position proximate said bore's upper end;

(c) a hollow sample tube coaxially disposable within, and substantially shorter than, said bore, said tube having an upper terminus, with a side vent, attachable to said piston, a lower terminus, and having a transversely and outwardly projecting flange, engageable with said rim, attached to said tube proximate said tube's upper terminus, said tube having an initial position disposed within said bore with said upper terminus attached to said piston and with said piston disposed at its upper position and said tube having a final position with said lower terminus disposed outside said bore in said sludge and with said flange disposed inside said bore contacting said rim, with said tube guidable by said flange from said initial position to said final position;

(d) means for temporarily holding said tube at its initial position, when said bore is generally vertically disposed, prior to moving said tube to its final position; and (e) means for rapidly accelerating said tube, by accelerating said piston, from said tube's initial position to said tube's final position such that when said tube's lower terminus reaches said sludge, said tube has a sufficient velocity to penetrate said sludge and obtain a full-length sludge sample, which retains strata information, before said tube stops with said flange stopped against said rim.

2. The system of claim 1, wherein said housing also includes means for entering said bore to load and unload said tube.

3. The system of claim 2, wherein said tube's flange is annular.

4. The system of claim 2, wherein said accelerating means includes compressed gas.

5. The system of claim 4, wherein said compressed gas originates from a compressed gas storage cylinder.

6. The system of claim 2, wherein said sludge is disposed in a tank having an accessible top.

7. The system of claim 6, wherein said sludge is radioactive and highly viscous.

8. The system of claim 7, also including means for remotely positioning said housing.

9. The system of claim 8, wherein said housing has a lifting bail and wherein said remote positioning means includes a hoist.

10. The system of claim 9, wherein said tube's flange is annular, said accelerating means includes compressed gas originating from a compressed gas storage cylinder, and wherein said tube is a copper tube about 1.3 meters long, 1.5 centimeters in outside diameter, 0.1 centimeter in wall thickness, and having a sludge entering velocity of from about 40 to 60 meters per second.

* * * * *